US011452452B2

(12) United States Patent
Takeno et al.

(10) Patent No.: US 11,452,452 B2
(45) Date of Patent: Sep. 27, 2022

(54) OCT SIGNAL PROCESSING DEVICE AND RECORDING MEDIUM

(71) Applicant: NIDEK CO., LTD., Gamagori (JP)

(72) Inventors: Naoki Takeno, Aichi (JP); Masaaki Hanebuchi, Aichi (JP); Yasuhiro Furuuchi, Aichi (JP); Hajime Namiki, Aichi (JP)

(73) Assignee: NIDEK CO., LTD., Gamagori (JP)

( * ) Notice: Subject to any disclaimer, the term of this patent is extended or adjusted under 35 U.S.C. 154(b) by 426 days.

(21) Appl. No.: 16/068,452

(22) PCT Filed: Jan. 5, 2017

(86) PCT No.: PCT/JP2017/000104
§ 371 (c)(1),
(2) Date: Oct. 22, 2018

(87) PCT Pub. No.: WO2017/119437
PCT Pub. Date: Jul. 13, 2017

(65) Prior Publication Data
US 2019/0380588 A1 Dec. 19, 2019

(30) Foreign Application Priority Data

Jan. 7, 2016 (JP) .............................. JP2016-002074

(51) Int. Cl.
*A61B 5/00* (2006.01)
*A61B 3/10* (2006.01)
(Continued)

(52) U.S. Cl.
CPC ............ *A61B 5/0066* (2013.01); *A61B 3/102* (2013.01); *A61B 3/12* (2013.01); *A61B 5/004* (2013.01);
(Continued)

(58) Field of Classification Search
CPC ......... A61B 5/0066; A61B 3/102; A61B 3/12; A61B 5/004; G06F 17/18; G06T 7/20;
(Continued)

(56) References Cited

U.S. PATENT DOCUMENTS

| 8,848,199 B2* | 9/2014 | Choi ..................... G01N 21/51 356/517 |
| 2004/0010375 A1* | 1/2004 | Schomacker ...... G01N 21/6456 702/19 |

(Continued)

FOREIGN PATENT DOCUMENTS

| JP | 2015-9108 A | 1/2015 |
| JP | 2015-29559 A | 2/2015 |
| JP | 2015-131107 A | 7/2015 |

OTHER PUBLICATIONS

Woojhon Choi, PhD, et al., "Ultrahigh Speed Swept Source OCT Angiography in Non-Exudative Age-Related Macular Degeneration with Geographic Atrophy", Available online: Oct. 18, 2015, American Academy of Ophthalmology, vol. 122, No. 12, pp. 2532-2544.
(Continued)

*Primary Examiner* — Joseph M Santos Rodriguez
*Assistant Examiner* — Kaitlyn E Sebastian
(74) *Attorney, Agent, or Firm* — Sughrue Mion, PLLC

(57) ABSTRACT

An OCT signal processing device has an acquisition unit for acquiring three or more OCT signals being temporally different from each other with respect to the same position on a subject, from an OCT device that detects an OCT signal based on reflection light of measurement light applied to a subject and reference light corresponding to the measurement light, and a calculation unit for calculating motion contrast based on a plurality of OCT signals. The calculation unit selects two or more sets of OCT signals having different time interval between the OCT signals among sets obtained by extracting a plurality of OCT signals out of the three or
(Continued)

more OCT signals, and calculates motion contrast for each of the selected two or more sets.

10 Claims, 7 Drawing Sheets

(51) Int. Cl.
*A61B 3/12* (2006.01)
*G06T 7/20* (2017.01)
*G06F 17/18* (2006.01)

(52) U.S. Cl.
CPC ............. *G06F 17/18* (2013.01); *G06T 7/20* (2013.01); *G06T 2207/10101* (2013.01)

(58) Field of Classification Search
CPC . G06T 2207/10101; G06T 2207/10016; G06T 2207/30041; G06T 5/003; G06T 5/50; G01N 21/17
See application file for complete search history.

(56) References Cited

U.S. PATENT DOCUMENTS

| | | | |
|---|---|---|---|
| 2014/0221827 A1* | 8/2014 | Motaghiannezam | ........................ A61B 5/1128 356/479 |
| 2015/0055089 A1 | 2/2015 | Aono et al. | |
| 2015/0168127 A1* | 6/2015 | Takeno | ................ A61B 5/0066 356/479 |
| 2016/0150954 A1* | 6/2016 | Furuuchi | .............. A61B 3/0025 351/206 |
| 2016/0183785 A1 | 6/2016 | Iwase et al. | |

OTHER PUBLICATIONS

JP Notification of Reasons for Revocation dated May 21, 2021 by the Japanese Patent Office in counterpart Japanese Patent Application No. 2017-560401.
Search Report dated Mar. 28, 2017, issued by the International Searching Authority in counterpart International Patent Application No. PCT/JP2017/000104 (PCT/ISA/210).
Written Opinion dated Mar. 28, 2017, issued by the International Searching Authority in counterpart International Patent Application No. PCT/JP2017/000104 (PCT/ISA/237).

* cited by examiner

[Fig. 1]
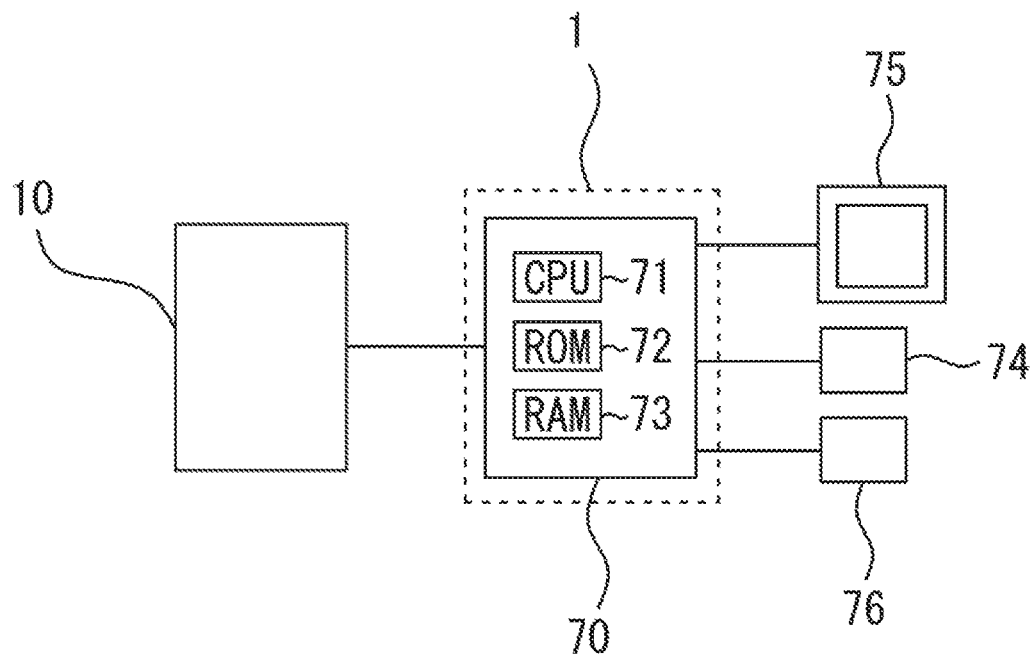
[Fig. 2]
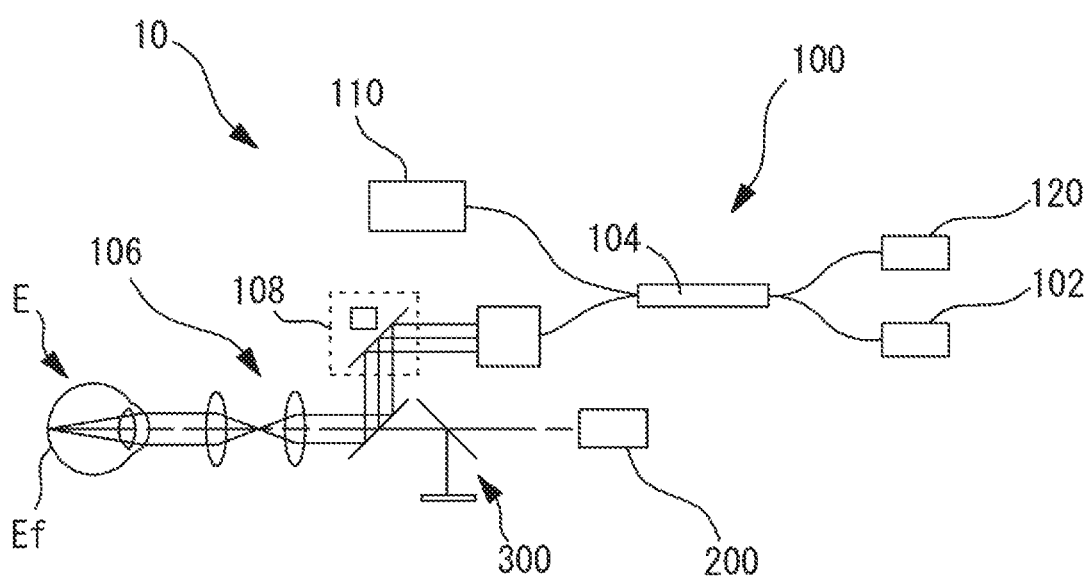

[Fig. 3]
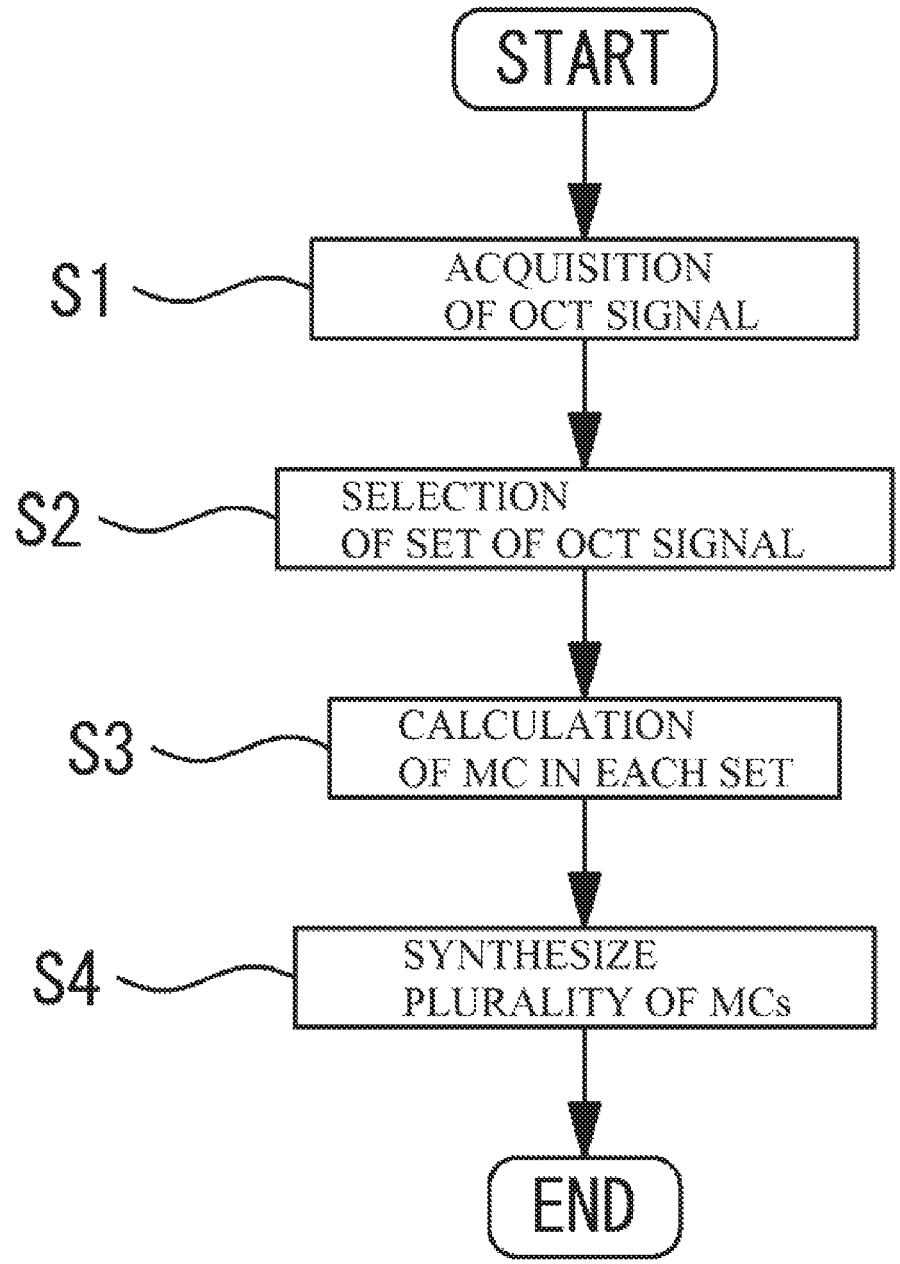

[Fig. 4]
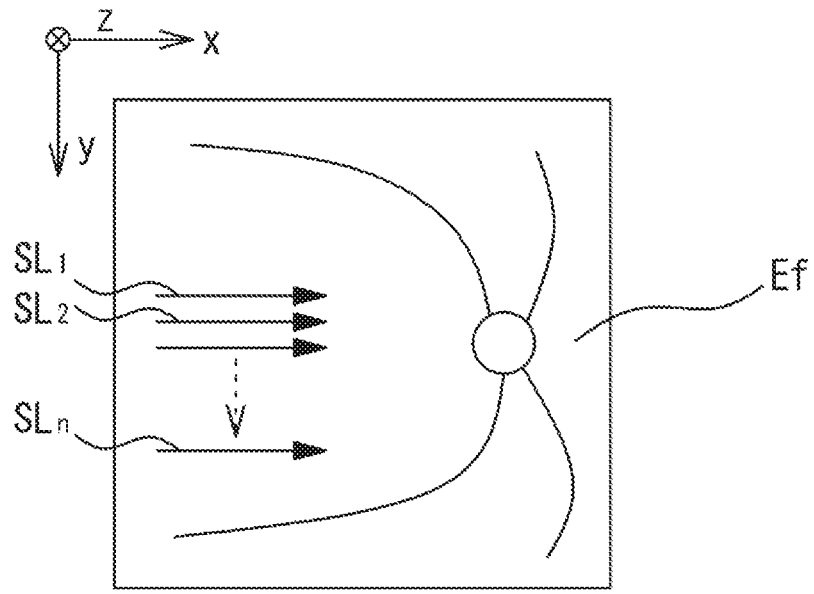
[Fig. 5]
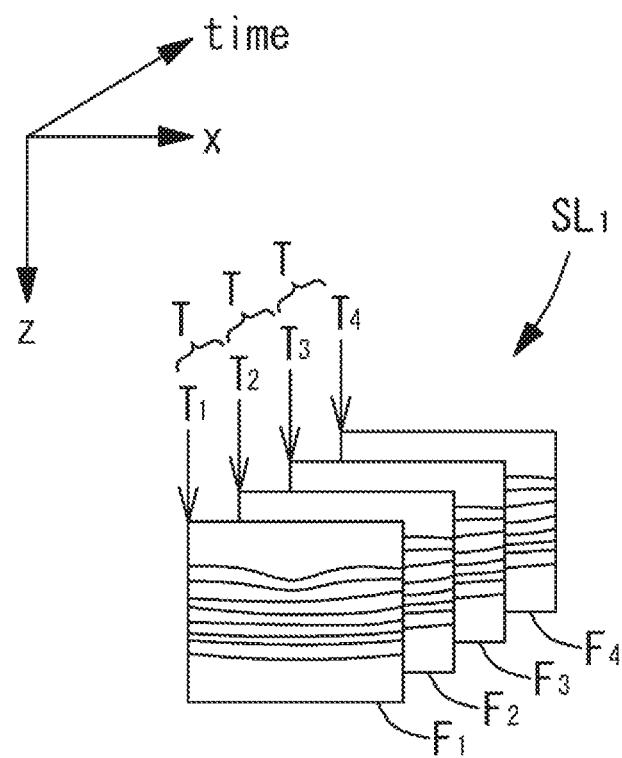

[Fig. 6A]
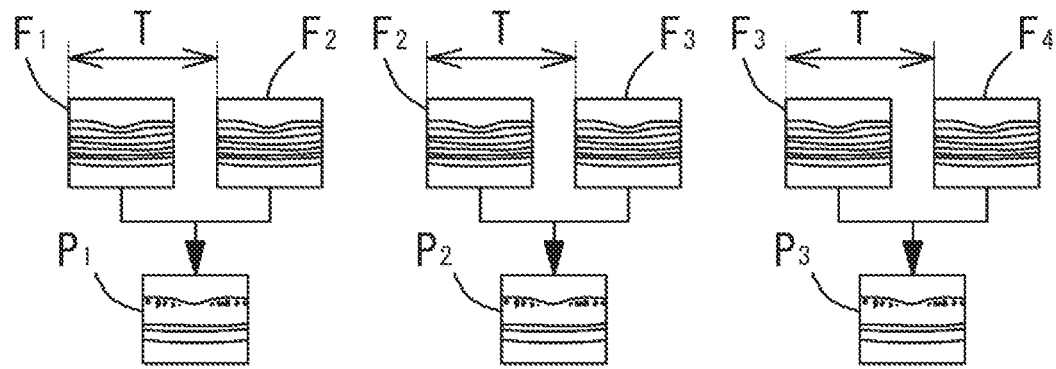
[Fig. 6B]
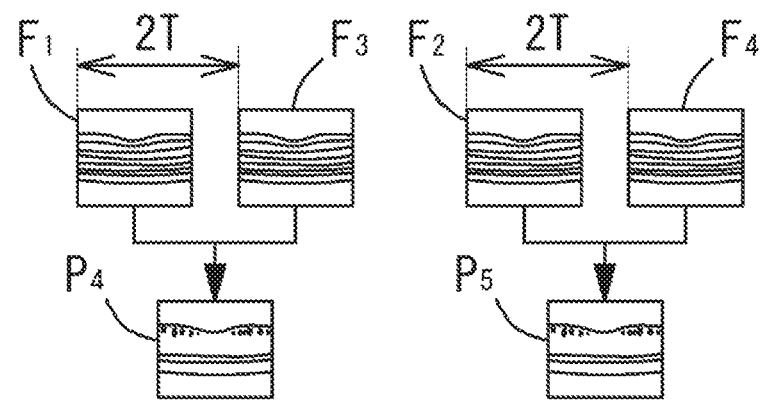
[Fig. 6C]
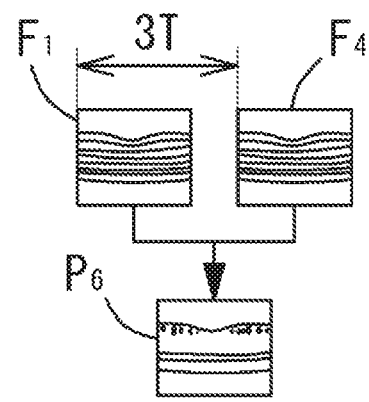

[Fig. 7]
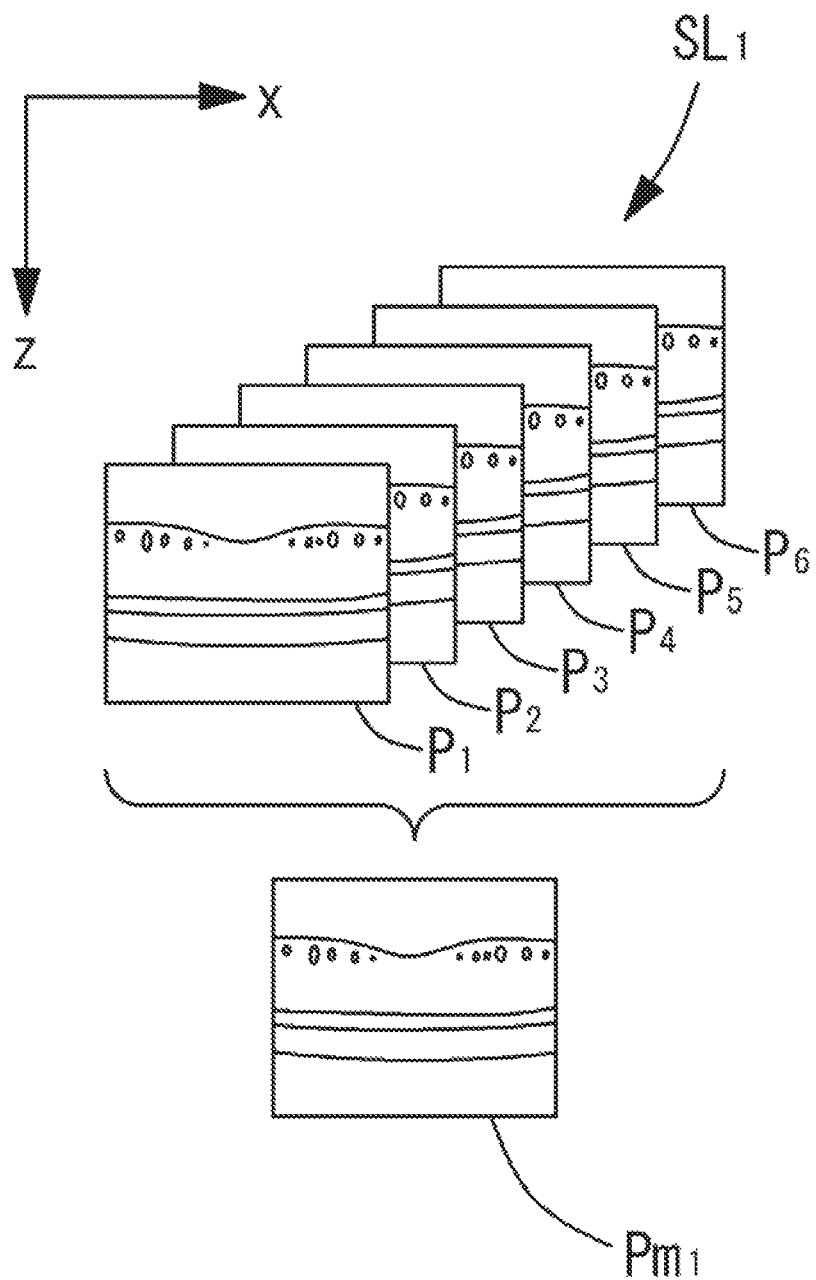

[Fig. 8A]
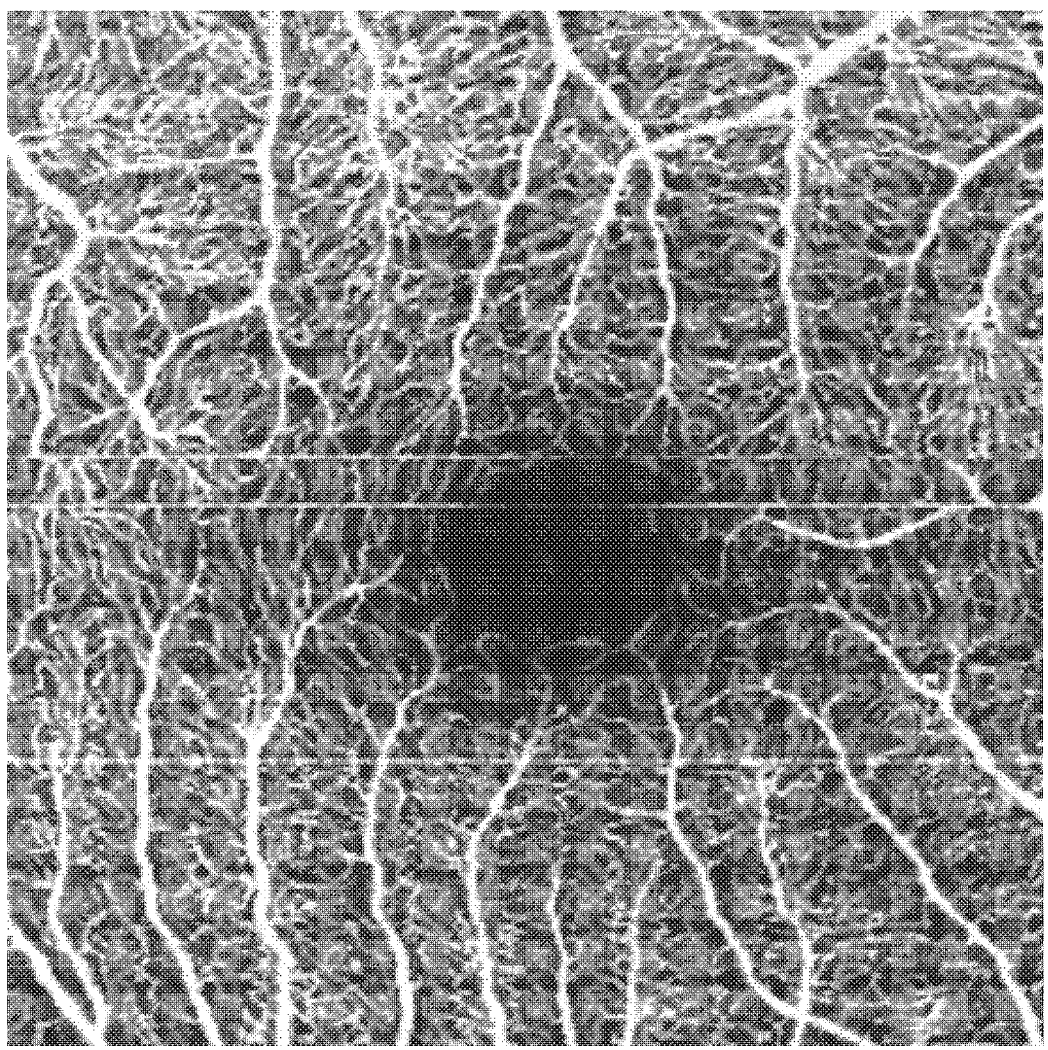

[Fig. 8B]
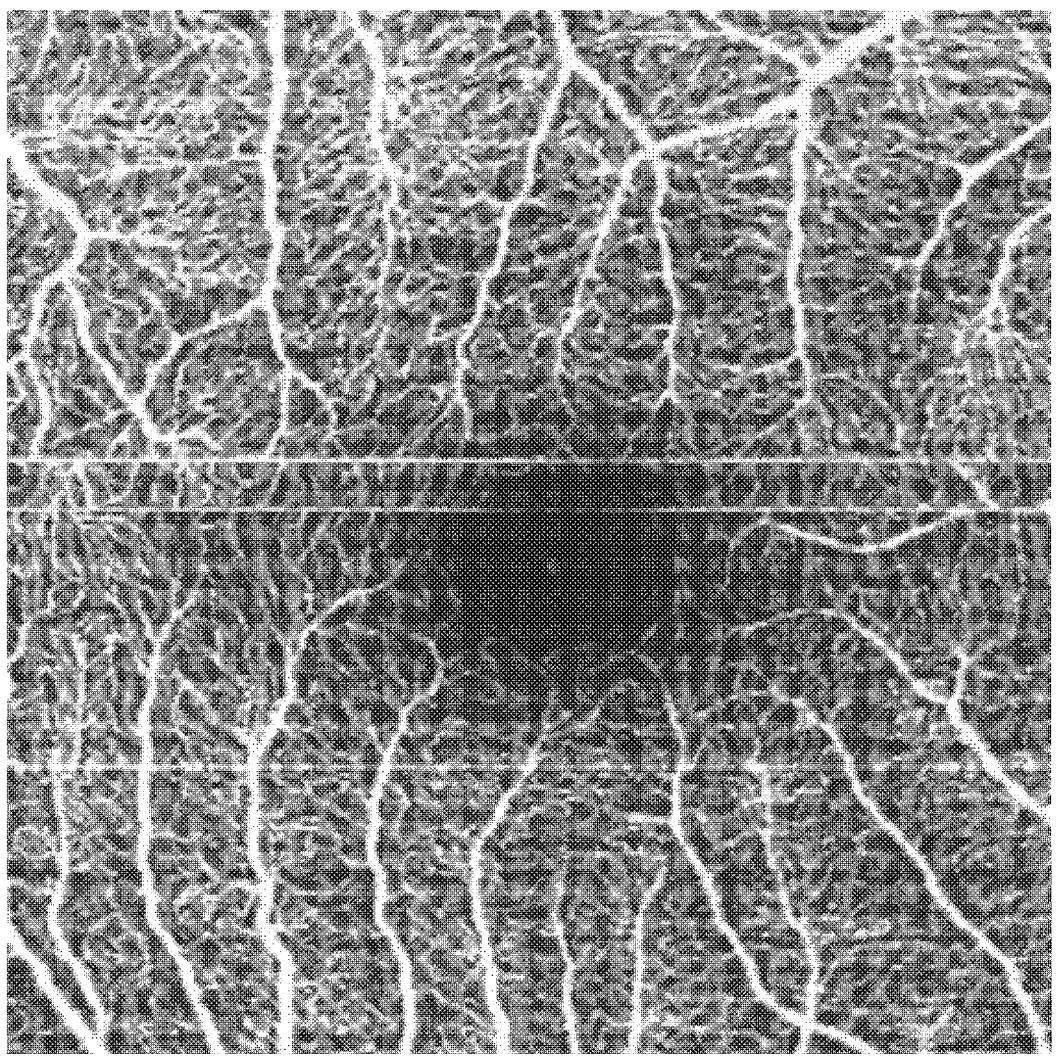

OCT SIGNAL PROCESSING DEVICE AND RECORDING MEDIUM

TECHNICAL FIELD

The present disclosure relates to an OCT signal processing device that processes an OCT signal acquired by an optical coherence tomography (OCT: Optical Coherence Tomography) and a recording medium storing an OCT signal processing program executed in the OCT signal processing device.

BACKGROUND ART

In the related art, an optical tomographic imaging device that acquires an optical interference tomographic image of a subject is known. The optical tomographic imaging device using an OCT divides light emitted from a light source into measurement light and reference light, and irradiates tissue of a subject with the divided measurement light while scanning the tissues. The measurement light reflected by the tissues is synthesized with the reference light, and information in a depth direction of the tissue is acquired from an interference signal of the synthesized light. The optical tomographic imaging device can generate a tomographic image by using the acquired information in the depth direction.

In addition, an acquisition of motion contrast of a subject by using the OCT is proposed (Refer to Patent Literature 1).

CITATION LIST

Patent Literature

Patent Literature 1: JP-A-2015 131107

SUMMARY OF INVENTION

Meanwhile, in order to obtain motion contrast of a subject, it is necessary to acquire a plurality of OCT signals that are temporally different at the same position, which takes time for measurement. However, in order to stabilize image quality of the motion contrast, it is necessary to acquire more OCT signals.

The present disclosure is to solve at least one of problems in the related art and is to provide an OCT signal processing device that can acquire a stable motion contrast, and a recording medium storing an OCT signal processing program executed in the OCT signal processing device.

In order to solve the above-described problems, the present disclosure has the following configuration.

(1) An OCT signal processing device, which processes an OCT signal, includes an acquisition unit for acquiring three or more OCT signals being temporally different from each other with respect to the same position on a subject, from an OCT device that detects an OCT signal based on reflection light of measurement light applied to a subject and reference light corresponding to the measurement light, and a calculation unit for calculating motion contrast, based on a plurality of OCT signals, in which the calculation unit selects two or more sets of OCT signals having different time interval between the OCT signals among sets obtained by extracting a plurality of OCT signals out of the three or more OCT signals, and calculates motion contrast for each of the selected two or more sets.

(2) An OCT signal processing device, which processes an OCT signal, includes an OCT device for detecting an OCT signal based on reflection light of measurement light applied to a subject and reference light corresponding to the measurement light, an acquisition unit for acquiring three or more OCT signals being temporally different from each other with respect to the same position on a subject from the OCT device, and a calculation unit for calculating motion contrast based on a plurality of OCT signals, in which the calculation unit selects two or more sets of OCT signals having different time interval between the OCT signals among sets obtained by extracting a plurality of OCT signals out of the three or more OCT signals, and calculates motion contrast for each of the selected two or more sets.

(3) A non-transitory computer readable recording medium storing an OCT signal processing program executed in an OCT signal processing device that processes an OCT signal in which the program is executed by a processor of the OCT signal processing device and causes the OCT signal processing device to perform an acquisition step of acquiring three or more OCT signals being temporally different from each other with respect to the same position on a subject, from an OCT device that detects an OCT signal based on reflection light of measurement light applied to a subject and reference light corresponding to the measurement light, and a calculation step of selecting two or more sets of OCT signals having different time interval between the OCT signals among sets obtained by extracting a plurality of OCT signals out of the three or more OCT signals, and calculating motion contrast for each of the selected two or more sets respectively.

BRIEF DESCRIPTION OF DRAWINGS

FIG. 1 is a block diagram illustrating the present embodiment.

FIG. 2 is a view illustrating an optical system of the present embodiment.

FIG. 3 is a flowchart illustrating a control operation of the present embodiment.

FIG. 4 is a diagram illustrating scan of a fundus of an eye.

FIG. 5 is a diagram illustrating OCT signals acquired at different times at the same position.

FIG. 6A is a diagram illustrating generation of motion contrast in a plurality of OCT signal pairs.

FIG. 6B is a diagram illustrating the generation of the motion contrast in the plurality of OCT signal pairs.

FIG. 6C is a diagram illustrating the generation of the motion contrast in the plurality of OCT signal pairs.

FIG. 7 is a diagram illustrating statistical processing of the motion contrast.

FIG. 8A is a view illustrating an example of motion contrast images processed differently from each other.

FIG. 8B is a view illustrating an example of the motion contrast images processed differently from each other.

DESCRIPTION OF EMBODIMENTS

Hereinafter, embodiments according to the present disclosure will be briefly described. An OCT signal processing device (for example, an OCT signal processing device 1) of the present embodiment processes, for example, an OCT signal. The OCT signal processing device includes, for example, a control unit 70, configured to function as an acquisition unit and a calculation unit. For example, the acquisition unit acquires three or more OCT signals different in time with respect to the same position on a subject from the OCT device (for example, an OCT device 10). The OCT device is, for example, a device that detects an OCT signal by scanning a subject with measurement light.

For example, the calculation unit calculates motion contrast, based on a plurality of OCT signals. The calculation unit selects two or more sets having different time intervals between the OCT signals, among sets obtained by extracting a plurality of OCT signals out of three or more OCT signals. Then, the calculation unit may calculate the motion contrast for each of the two or more selected sets. The time interval is, for example, a time interval between timing at which one OCT signal is detected and timing at which the other OCT signal is detected.

The calculation unit may synthesize the calculated motion contrast with each of two or more sets. For example, a third motion contrast may be calculated by synthesizing a first motion contrast calculated from a first set with a second motion contrast calculated from a second set.

The calculation unit may synthesize the selected motion contrast (MC), based on an evaluation index relating to motion contrast from among the motion contrasts calculated for each of the two or more sets. For example, the calculation unit may select and synthesize the motion contrast with a relatively high signal-to-noise (SN) ratio from among the motion contrast calculated for each of the two or more sets. The calculation unit may use a ratio between an integral value of an intensity image of a certain scan line and an integral value of an MC image as an evaluation index.

The calculation unit may calculate the motion contrast for each of all sets that can be selected from three or more OCT signals. For example, the motion contrast may be calculated for all sets acquired by combination processing.

The calculation unit may synthesize the motion contrast calculated for each of the two or more sets by statistical processing. For example, the calculation unit may synthesize the motion contrast calculated for each of the two or more sets by statistical processing in which any one of an addition average value, a median value, a maximum value, a minimum value, and the like is used.

The calculation unit may assign weights to the statistical processing according to lengths of the two or more sets of time intervals. For example, the calculation unit may perform the statistical processing by reducing a weight of a set of the motion contrasts having a long time interval.

The calculation unit may change a calculation method of the motion contrast in each set depending on a length of the time interval. For example, a parameter and the like used for the calculation may be changed depending on the length of the time interval. Accordingly, the motion contrast suitable for the time interval may be calculated. Of course, the calculation method may be the same.

The acquisition unit may acquire OCT signals sequentially detected at a constant time interval.

A processor (for example, a CPU 71) of the OCT signal processing device may execute an OCT signal processing program stored in a storage unit (for example, a storage unit 74). The OCT signal processing program includes, for example, an acquisition step and a calculation step. The acquisition step is a step of acquiring three or more OCT signals which are different in time with respect to the same position of a subject, from the OCT device that detects the OCT signals by scanning a subject with measurement light. In the calculation step is a step of selecting two or more sets of the OCT signals with different time intervals, and calculating the motion contrast for each of the selected two or more sets, for example, among the sets obtained by extracting a plurality of OCT signals out of three or more OCT signals.

<Embodiment>

Hereinafter, the OCT signal processing device of the present embodiment will be described with reference to the drawings. The OCT signal processing device 1 illustrated in FIG. 1 performs analysis processing of the OCT signal acquired by the OCT device 10. For example, the OCT signal processing device processes the OCT signal and calculates the motion contrast (hereinafter, there is a case of being abbreviated as MC).

The OCT analysis device 1 includes, for example, the control unit 70. The control unit 70 is realized by, for example, a general CPU (Central Processing Unit) 71, a ROM 72, a RAM 73, and the like. The ROM 72 stores, for example, an analysis processing program for processing the OCT signal, a program for controlling an operation of the OCT device 10 to obtain motion contrast data, an initial value, and the like. The RAM 73 temporarily stores, for example, various types of information.

As illustrated in FIG. 1, for example, the storage unit (for example, a nonvolatile memory) 74, an operation unit 76, a display unit 75, and the like are electrically connected to the control unit 70. The storage unit 74 is, for example, a non-transitory storage medium capable of holding stored contents even when supply of power is cut off. For example, a hard disk drive, a flash ROM, a detachable USB memory, or the like can be used as the storage unit 74.

Various operation instructions provided by an examiner are input to the operation unit 76. The operation unit 76 outputs a signal according to the input operation instruction to the CPU 71. At least one user interface such as a mouse, a joystick, a keyboard, a touch panel, or the like may be used as the operation unit 76.

The display unit 75 may be a display mounted on a main body of the device 1 or may be a display connected to the main body. For example, a display of a personal computer (hereinafter, referred to as a "PC") may be used. The display unit 75 displays, for example, OCT data, motion contrast data, and the like acquired by the OCT device 10.

The OCT signal processing device 1 of the present embodiment is connected to, for example, the OCT device 10. The OCT signal processing device 1 may have, for example, an integrated structure with the OCT device 10, which is housed in the same case or may have a separate configuration. The control unit 70 may acquire the motion contrast data from the connected OCT device 10. The control unit 70 may acquire the motion contrast data acquired by the OCT device 10 via the storage medium.

<OCT Device>

Hereinafter, an outline of the OCT device 10 will be described with reference to FIG. 2. For example, the OCT device 10 irradiates a subject eye E with the measurement light, and acquires an OCT signal acquired by the reflection light and reference light. The OCT device 10 mainly includes, for example, an OCT optical system 100.

<OCT Optical System>

The OCT optical system 100 irradiates a subject eye E with the measurement light and detects an interference signal between the reflection light and the reference light. The OCT optical system 100 mainly includes, for example, a measurement light source 102, a coupler (optical divider) 104, a measurement optical system 106, a reference optical system 110, a detector 120, and the like. For a detailed configuration of the OCT optical system, for example, JP-A-2015-131107 may be referred to.

The OCT optical system 100 is an optical system of a so-called optical coherence tomography (OCT). The OCT optical system 100 divides the light emitted from the measurement light source 102 into measurement light (sample light) and reference light by using a coupler 104. The divided measurement light is guided to a measurement optical system 106, and the reference light is guided to a reference optical system 110. The measurement light is guided to a fundus Ef of the subject eye E through the measurement optical system 106. Thereafter, a detector 120 receives interference light resulting from synthesis of the measurement light reflected by the subject eye E and the reference light.

The measurement optical system 106 may include, for example, a scan unit (for example, an optical scanner) 108. For example, the scan unit 108 may be provided to scan (scan) measurement light in the X and Y directions (transverse direction) on the fundus. For example, the CPU 71 controls an operation of the scan unit 108, based on the set scan position information, and acquires the OCT signal, based on a light reception signal detected by the detector 120. Of course, the measurement optical system 106 may be configured without the scan unit 108. In this case, the measurement optical system 106 may be configured to apply regionally the measurement light once. The reference optical system 110 generates the reference light synthesized with the reflection light to be acquired by the reflection of the measurement light in the fundus Ef. The reference optical system 110 may be a Michelson type or a Mach-Zehnder type.

The detector 120 detects an interference state between the measurement light and the reference light. In a case of a Fourier domain OCT, a spectral intensity of the interference light is detected by the detector 120, and a depth profile (A scan signal) in a predetermined range is acquired by Fourier transform on the spectral intensity data.

For example, Spectral-domain OCT (SD-OCT), Swept-source OCT (SS-OCT), Time-domain OCT (TD-OCT), or the like may be used as the OCT device 10.

<Front Imaging Optical System>

For example, a front imaging optical system 200 images the fundus Ef of the subject eye E from the front direction (for example, an optical axis direction of the measurement light) to obtain a front image of the fundus Ef. For example, the front imaging optical system 200 may have a device configuration of a scan type laser ophthalmoscope (SLO) (refer to, for example, JP-A-2015-66242), or may have a configuration of a so-called fundus camera type (refer to JP-A-2011-10944). The OCT optical system 100 may also be used as the front imaging optical system 200, and a front image may be acquired based on a detection signal from the detector 120.

<Fixation Target Projection Unit>

A fixation target projection unit 300 includes an optical system for guiding a visual line direction of the eye E. The projection unit 300 includes a fixation target presented to the eye E and can guide the eye E. For example, the fixation target projection unit 300 includes a visible light source that emits visible light, and two-dimensionally changes a presentation position of the fixation target. Thereby, the visual line direction is changed, and as a result, an acquisition position of the OCT data is changed.

<Control Operation>

A control operation when the OCT signal acquired by the OCT device 10 is processed in the OCT signal processing device 1 having the above-described configuration will be described with reference to FIG. 3. In the following description, a case where the subject eye E is measured by the OCT device 10 and the acquired OCT signal is processed to calculate the motion contrast will be described.

<Step S1: Acquisition of OCT Signal>

First, the OCT signal processing device 1 acquires an OCT signal. For example, the CPU 71 acquires the OCT signal detected by the OCT device 10 and stores the data in the storage unit 74 or the like. In the following description, for example, the CPU 71 controls the OCT device 10 to acquire the OCT signal, but a control unit may be individually provided in the OCT device 10.

Hereinafter, a method of detecting the OCT signal by using the OCT device 10 will be described. For example, the CPU 71 controls the fixation target projection unit 300 to project a fixation target to an examinee. Then, the CPU 71 controls a drive portion not illustrated to automatically perform alignment such that the measurement a measurement optical axis is at the center of a pupil of the subject eye E, based on a front eye portion observation image captured by a front eye portion observation camera not illustrated.

If the alignment is completed, the OCT device 10 measures the subject eye E. For example, the OCT device 10 acquires at least two OCT signals that differ in time with respect to the same position on the subject eye. For example, the CPU 71 controls drive of an optical scanner 108 to scan the measurement light on the fundus. At this time, for example, the measurement light is scanned in the x direction along a scan line SL1 illustrated in FIG. 4. Scanning the measurement light in a direction (for example, the x direction) crossing the optical axis direction of the measurement light is referred to as "B scan". Then, an OCT signal obtained by B scan of one time will be described as an OCT signal of one frame. In FIG. 4, a direction of the z axis is set as an optical axis direction of the measurement light. A direction of the x axis is perpendicular to the z-axis and is set as a left-right direction of an examinee. A direction of the y axis is perpendicular to the z axis and is set as an up-down direction of the examinee.

While scanning the measurement light, the CPU 71 acquires the OCT signal detected by the detector 120. If a first scan is completed at time T1, the CPU 71 performs a second scan at time T2 when a predetermined time interval (time interval) elapses from the time T1 at the same scan position as the first time. For example, the CPU 71 scans the measurement light along the scan line SL1 illustrated in FIG. 4 and then, causes the measurement light to be scanned again along the scan line SL1. The CPU 71 acquires the OCT signal detected by the detector 120 during scan of the measurement light. Thereby, the CPU 71 can acquire the OCT signals of two frames having different detection times at the same scan position.

For example, the CPU 71 repeats scan at the same position by N (a natural number of 2 or more) times and acquires an OCT signal of consecutive N frames at a predetermined scan time interval. For example, the CPU 71 repeats the scan on the scan line SL1 N times to acquire the OCT signal of N frames. In this way, the CPU 71 acquires the OCT signal of two or more frames having different times. In the present embodiment, a case where scanning at the same position is repeated four times will be described.

For example, as illustrated in FIG. 5, an image based on an OCT signal detected when the scan line SL1 is scanned at the time T1 is referred to as an image F1, an image based on the OCT signal detected at the time T2 is referred to as an image F2, an image based on the OCT signal detected at time T3 is referred to as an image F3, and an image based on the OCT signal detected at time T4 is referred to as an image F4. Each time interval between the time T1, the time T2, the time T3, and the time T4 is time T.

<Step S2: Selection of Set of OCT Signals>

In order to acquire the motion contrast, at least two OCT signals detected at different times at the same position are used. Accordingly, for example, the CPU 71 selects a set including at least two OCT signals from among a plurality of OCT signals detected at different times at the same position. For example, the two OCT signals may be temporally adjacent sets or may be temporally separated sets. That is, a set in which a time interval (time interval) between timing when one OCT signal is detected and timing when the other OCT signal is detected is the shortest may be selected, or a set that is not the shortest may be selected. The CPU 71 may select a plurality of pairs. At this time, time intervals of the plurality of pairs may be different from each other.

For example, the CPU 71 may perform B scans of different times N times to acquire N OCT signals. For example, in a case where two signals are selected from the N OCT signals, the CPU 71 can select $_NC_2$ pairs as represented by the following equation (1).

$$_NC_2 = \frac{N(N-1)}{2} \quad (1)$$

For example, Table 1 illustrates the number of pairs at the shortest time interval (for example, scan time interval) T considered in a case where the number (the number of captured images) of scans of the measurement light is from 2 to 8, and the number of pairs of the OCT signals obtained from combination processing of the equation (1), regardless of the time interval.

TABLE 1

| Number of imaging at the same position | Pair at the shortest time interval | Pair by combination |
|---|---|---|
| 2 | 1 | 1 |
| 3 | 2 | 3 |
| 4 | 3 | 6 |
| 5 | 4 | 10 |
| 6 | 5 | 15 |
| 7 | 6 | 21 |
| 8 | 7 | 28 |

For example, in order to obtain six pairs of OCT signals, imaging of seven times is required in a case where only the pair at the shortest time interval T is selected, but only imaging of four times are required in a case where a pair by combination is selected.

In addition, when imaging of eight times is performed and eight OCT signals are acquired, seven motion contrasts are acquired at the shortest time interval T, but 28 pairs of motion contrasts of maximum $_8C_2$ are acquired by combination.

The CPU 71 may select all the sets that can be selected or may select a part of the sets.

<S3: MC Calculation in Each Set>

For example, the CPU 71 calculates the motion contrast for each set of the selected OCT signal. For example, the CPU 71 processes each OCT signal and acquires a complex OCT signal. For example, the CPU 71 performs Fourier transform of the OCT signal. For example, if a signal at a position (x,z) of an nth frame out of N frames is represented as An(x,z), the CPU 71 obtains a complex OCT signal An(x,z) through the Fourier transform. The complex OCT signal An(x,z) includes a real component and an imaginary component.

The CPU 71 processes the acquired complex OCT signal and obtains the motion contrast. The method of processing the complex OCT signal includes, for example, a method of calculating an intensity difference between the complex OCT signal, a method of calculating dispersion of intensities of the complex OCT signals, a method of calculating a phase difference between the complex OCT signals, a method of calculating a vector difference between the complex OCT signals, a method (correlation mapping, decorrelation mapping) of using correlation (or decorrelation) between the OCT signals, and a method of combining motion contrast data obtained thereby. In the present embodiment, the method of calculating the phase difference will be described as an example.

The CPU 71 calculates a phase change of each OCT signal pair using, for example, the following equation (2). In the equation, An indicates a signal acquired at time Tn, Am indicates a signal acquired at time Tm, and * indicates a complex conjugate.

$$\Delta\Phi_{n,m}(x,z) = \arg(A_m(x,z) \times A_n^*(x,z))(n<m) \quad (2)$$

As described above, the CPU 71 acquires a phase difference profile in a depth direction (A scan direction) with respect to the phase difference between the complex OCT signal. For example, the CPU 71 obtains a luminance profile in which a magnitude of luminance is determined according to a magnitude of the phase difference profile, and acquires a two-dimensional image in which the luminance profile is arranged in the B scan direction. In the same manner as described above, the CPU 71 calculates the motion contrast also in another set and stores a plurality of the obtained motion contrasts in the storage unit 74 or the like.

For example, in a case where the number of scans is 4 and the motion contrast is calculated based on all pairs that can be selected, six motion contrasts illustrated in FIGS. 6A and 6B are calculated. The images P1, P2, P3 in FIG. 6A are the motion contrasts based on pairs acquired at an interval equal to the shortest time interval T. Images P4, P5 in FIG. 6B are motion contrasts based on pairs acquired at an interval which is twice the shortest time interval T, an image P6 in FIG. 6C is motion contrast based on the pair acquired at an interval which is three times the shortest time interval T.

<S4: Synthesis of Plural MCs>

Next, the CPU 71 synthesizes the motion contrasts calculated for each of the plurality of sets in the statistical processing. For example, calculation processing of an addition average value, a median value, a maximum value, a minimum value, and the like can be used as the statistical processing.

For example, the CPU 71 synthesizes the motion contrast calculated based on a plurality of sets by adding and averaging. For example, as illustrated in FIG. 7, a plurality of motion contrasts (for example, images P1 to P6) are added and averaged based on pairs with different time intervals and are synthesized as one motion contrast Pm1.

In this way, the CPU 71 selects a plurality of OCT signals from, for example, a plurality of OCT signals sequentially detected during scan at a constant time interval regardless of a temporal sequence, and calculates the motion contrast of the selected set.

The CPU 71 may acquire the motion contrast at each of the scan positions SL1 to SLn as described above, and may acquire three-dimensional motion contrast data.

As described above, by calculating the motion contrast from a plurality of sets selected from a plurality of OCT signals, more motion contrasts can be acquired with respect to the number of scans (the number of captured images). For example, in a case where N OCT signals are acquired, the CPU 71 acquires (N−1) motion contrasts in a case where the set of the shortest time interval T is selected, but the CPU can acquire N(N−1)/2 motion contrasts in a case where the set is selected regardless of the time interval. That is, even when the same number of captured images is taken, in a case where the set is selected regardless of the time interval, it is possible to calculate more motion contrasts than a case where the set of the shortest time intervals T is selected. Therefore, it is possible to acquire a large number of motion contrasts at a small number of scan times. Thereby, measurement time can be reduced.

For example, FIG. 8A is an image when six frames of the motion contrast of the shortest time interval are added in a case where the number of scans is seven, and FIG. 8B is an image when six frames of the motion contrast of a plurality of time intervals are added in the same way in a case where the number of scans is four. As illustrated in FIGS. 8A and 8B, even in a case where the number of scans is reduced it is possible to acquire the motion contrast which is the same as the motion contrast before the number of scans is reduced, by selecting a set regardless of the time interval.

Since it is expected that the SN ratio is increased by statistically processing a large number of data in the motion contrast, it is more advantageous to calculate the motion contrast even in the set selected regardless of the time interval as in the present embodiment.

The CPU 71 can acquire the motion contrast at a plurality of time intervals by using the OCT signal detected at a constant scan time interval. That is, since the time interval changes depending on each set, a blood vessel with different blood flow velocities can be detected as motion contrast. For example, if the time interval is short, a blood vessel in which blood flows fast is detected, and if the time interval is long, a blood vessel in which blood flows slowly is detected. Therefore, the OCT signal processing device 1 of the present embodiment can acquire the motion contrast on a plurality of kinds of blood vessels without changing a scan time interval of the OCT device 10.

The CPU 71 may perform the statistical processing by using one set with a high SN ratio out of a plurality of sets. For example, the CPU 71 calculates a median value of luminance from retinal areas of each motion contrast calculated from the plurality of sets. Then, the CPU 71 may set an average value +2σ (σ: standard deviation) of the median values as a threshold value, may remove the motion contrast having a luminance value higher than that as a bad SN ratio, and may perform the statistical processing with the remaining motion contrast. By doing so, motion contrast with a high SN ratio can be acquired.

The SN ratio tends to be worse in a set (for example, the OCT signal detected by the first scan and the OCT signal detected by the last scan) having a long time interval. This is because there is a high possibility that a position of a subject eye is shifted between the first scan and the last scan time. Therefore, the statistical processing may be weighted according to the time interval. For example, the statistical processing may be performed by increasing the weighting of the set of motion contrasts with a short time interval and decreasing the weighting of the set of motion contrasts with a long time interval. By doing so, motion contrast with a high SN ratio can be acquired.

The CPU 71 may change calculation processing of the motion contrast according to a length of the time interval. For example, the magnitude of the threshold value for removing a noise floor may be changed depending on the time interval. Of course, the motion contrast may be calculated by performing constant processing regardless of the length of the time interval.

In the above-described embodiments, the CPU 71 acquires the motion contrast by combining all sets, but may acquire the motion contrast by combining only a part of the sets.

When the same scan position is scanned a plurality of times, the scan time interval may be constant each time the number of scans is changed, or may be changed. That is, the time interval between the first scan and the second scan and the time interval between the second scan and the third scan may be equal to each other or may be changed.

In a case where B scan is performed a plurality of times for the same part, tracking may be performed for the fundus Ef of a subject eye. For example, a position of the B scan may be corrected based on shift information of a front image of the fundus captured at a predetermined interval by an observation optical system.

Although the OCT device 10 measures the subject eye E, a subject to be examined is not limited to the subject eye E and may be another portion of a living body or may be a substance.

In a case where two or more signals can be acquired by one scan at the same position at different times, it is not necessary to perform a second scan. For example, in a case where two measurement light beams whose optical axes are shifted by a predetermined interval are scanned once, it is not necessary to scan a plurality of times. It is only necessary to acquire the OCT signal with different times at the same position of a subject to be examined (Refer to JP-A-2013-7601).

REFERENCE SIGNS LIST

1 OCT signal processing device
10 OCT device
70 control unit
71 CPU
74 storage unit
75 display unit

The invention claimed is:
1. An optical coherence tomography (OCT) signal processing device configured to process an OCT signal, comprising:
a central processing unit (CPU) configured to:
acquire three or more OCT signals, each of the three or more OCT signals being temporally different from each other with respect to a same position on a subject, from an OCT device that detects OCT signals based on reflection light of measurement light applied to the subject and reference light corresponding to the measurement light;
extract a plurality of OCT signals from the three or more OCT signals;
select two or more sets of OCT signals from the plurality of OCT signals, the two or more sets of OCT signals having different time intervals, and calculate motion contrast for each of the selected two or more sets,
wherein the two or more sets of OCT signals having different time intervals include a temporally separated set of extracted OCT signals which are not temporally adjacent, and
wherein the CPU is further configured to synthesize motion contrasts calculated for each of the two or more sets.

2. The OCT signal processing device according to claim 1,
wherein the CPU is further configured to synthesize the motion contrasts calculated for each of the two or more sets based on an evaluation index relating to the motion contrast from among motion contrasts calculated for each of the two or more sets.

3. The OCT signal processing device according claim 1,
wherein CPU is further configured to calculate motion contrast for each of all sets that is able to be selected from among the three or more OCT signals.

4. The OCT signal processing device according claim 1,
wherein the CPU is further configured to synthesize motion contrasts calculated for each of the two or more sets through statistical processing.

5. The OCT signal processing device according to claim 4,
wherein the CPU is further configured to assign weights to the statistical processing according to lengths of time intervals of the two or more sets.

6. The OCT signal processing device according to claim 1,
wherein the CPU is further configured to change a calculation method of motion contrast in each set according to a length of the time interval.

7. An optical coherence tomography (OCT) signal processing device configured to process OCT signals, comprising:
an OCT device for detecting OCT signals based on reflection light of measurement light applied to a subject and reference light corresponding to the measurement light; and
a central processing unit (CPU) configured to:
acquire three or more OCT signals, each of the three or more OCT signals being temporally different from each other with respect to a same position on the subject from the OCT device;
extract a plurality of OCT signals from the three or more OCT signals;
select two or more sets of OCT signals from the plurality of OCT signals, the two or more sets of OCT signals having different time intervals, and calculate motion contrast for each of the selected two or more sets,
wherein the two or more sets of OCT signals having different time intervals include a temporally separated set of extracted OCT signals which are not temporally adjacent, and
wherein the CPU is further configured to synthesize motion contrasts calculated for each of the two or more sets.

8. A non-transitory computer readable recording medium storing an optical coherence tomography (OCT) signal processing program configured to be executed in an OCT signal processing device that processes OCT signals, the program being configured to be executed by a processor of the OCT signal processing device and cause the OCT signal processing device to perform:
acquisition of three or more OCT signals, each of the three or more OCT signals being temporally different from each other with respect to a same position on a subject, from an OCT device that detects an OCT signal based on reflection light of measurement light applied to a subject and reference light corresponding to the measurement light;
extraction of a plurality of OCT signals from the three or more OCT signals;
selection of two or more sets of OCT signals from the plurality of OCT signals, the two or more sets of OCT signals having different time intervals and calculation of motion contrast for each of the selected two or more sets respectively,
wherein the two or more sets of OCT signals having different time intervals include a temporally separated set of extracted OCT signals which are not temporally adjacent, and
wherein the CPU is further configured to synthesize motion contrasts calculated for each of the two or more sets.

9. The OCT signal processing device according to claim 1,
wherein the CPU is further configured to select a set of OCT signals having a time interval other than a shortest time interval.

10. The OCT signal processing device according to claim 1, wherein a first set of OCT signals included in the two or more sets of OCT signals is configured by a plurality of OCT signals having a first time interval, a second set of OCT signals included in the two or more sets of OCT signals is configured by a plurality of OCT signals having a second time interval, and the first interval and the second interval are different from each other at a ratio of one to an integer of two or more.

* * * * *